US010932834B2

(12) United States Patent
Stupak (10) Patent No.: US 10,932,834 B2
(45) Date of Patent: Mar. 2, 2021

(54) OBLIQUE THREE-DIMENSIONAL PLATE (71) Applicant: Howard D. Stupak, Southport, CT (US)

(72) Inventor: Howard D. Stupak, Southport, CT (US)

(*) Notice: Subject to any disclaimer, the term of this patent is extended or adjusted under 35 U.S.C. 154(b) by 237 days.

(21) Appl. No.: 15/367,695

(22) Filed: Dec. 2, 2016

(65) Prior Publication Data
US 2017/0156770 A1 Jun. 8, 2017

Related U.S. Application Data (60) Provisional application No. 62/386,493, filed on Dec. 3, 2015.

(51) Int. Cl.
*A61B 17/80* (2006.01)
*A61B 17/58* (2006.01)

(52) U.S. Cl.
CPC .............. *A61B 17/8085* (2013.01)

(58) Field of Classification Search
CPC . A61B 17/8085; A61B 17/8061; A61B 17/80; A61B 17/84; A61B 17/8071
USPC ................... 606/70–71, 280–299
See application file for complete search history.

(56) References Cited

U.S. PATENT DOCUMENTS

| | | | | |
|---|---|---|---|---|
| 4,905,679 A * | 3/1990 | Morgan | ............. | A61B 17/8085 227/156 |
| 5,690,631 A * | 11/1997 | Duncan | ............. | A61B 17/8085 606/281 |
| 5,752,958 A * | 5/1998 | Wellisz | ............. | A61B 17/8085 606/280 |
| 5,766,176 A * | 6/1998 | Duncan | ............. | A61B 17/8085 606/281 |
| 5,814,048 A * | 9/1998 | Morgan | ............. | A61B 17/8085 606/283 |
| 5,980,540 A * | 11/1999 | Bruce | ................ | A61B 17/8085 606/151 |
| 6,692,498 B1 * | 2/2004 | Niiranen | ................ | A61B 17/80 606/70 |
| 7,077,844 B2 * | 7/2006 | Michelson | ......... | A61B 17/1604 606/247 |
| 8,246,663 B2 * | 8/2012 | Lovald | ............... | A61B 17/8071 606/280 |
| 10,076,416 B2 * | 9/2018 | Engstrand | ............. | A61F 2/2846 623/17.19 |
| 2005/0149032 A1 * | 7/2005 | Vaughen | ............. | A61B 17/8085 606/77 |
| 2005/0261780 A1 * | 11/2005 | Heino | ................ | A61B 17/8085 623/23.51 |
| 2005/0273104 A1 * | 12/2005 | Oepen | ................ | A61B 17/8085 606/285 |
| 2005/0288790 A1 * | 12/2005 | Swords | ............. | A61B 17/8085 623/17.19 |
| 2007/0156146 A1 * | 7/2007 | Metzger | ............. | A61B 17/8061 606/86 A |
| 2007/0238069 A1 * | 10/2007 | Lovald | ............... | A61B 17/8071 433/173 |

(Continued)

*Primary Examiner* — Jessica Weiss
(74) *Attorney, Agent, or Firm* — K&L Gates LLP (57) ABSTRACT A three-dimensional mini-plate with an oblique orientation for use in immobilizing fractures in facial bones such as the mandible. The plate's oblique orientation permits it to be better matched to oblique fractures such that its edges do not interfere with tooth roots or the inferior margin of the mandible.

7 Claims, 10 Drawing Sheets (56) References Cited

U.S. PATENT DOCUMENTS

| | | | |
|---|---|---|---|
| 2012/0010617 A1* | 1/2012 | Ramos Maza | A61B 17/1746 606/70 |
| 2013/0245699 A1* | 9/2013 | Orbay | A61B 17/8061 606/286 |
| 2014/0316472 A1* | 10/2014 | Rise | A61B 17/8085 606/281 |
| 2015/0313652 A1* | 11/2015 | Burckhardt | A61B 17/80 606/71 |
| 2015/0374497 A1* | 12/2015 | Engstrand | A61F 2/2846 623/17.19 |

* cited by examiner

OBLIQUE THREE-DIMENSIONAL PLATE

CROSS REFERENCE TO RELATED APPLICATIONS

The present application claims priority to U.S. Patent Application No. 62/386,493, filed Dec. 4, 2015, titled "Vertical Oblique Tapered Plates," the disclosure of which is hereby incorporated by reference in its entirety.

BACKGROUND OF THE INVENTION

Field of the Invention

Disclosed herein are plates designed to treat mandible and facial fractures by improving the technique of plating such fractures.

Those skilled in the art of treating fractures of the mandible are familiar with the current techniques in repairing mandible and other facial fractures. Rectangular or square three dimensional mini-plates were introduced by Farmand in 1992 to prevent torsion of fractured mandibular segments in response to the twisting or rotational forces upon the mandible that are not prevented with single plate reduction. The 3D mini-plate is essentially two conventional mini-plates joined by bars. It permits the use of a single plate to achieve vertical stability and prevent torsion. This is especially important in the case of two or more fractures, where a free floating segment of the mandible is particularly at risk for twisting or torsion (Ellis, J Oral Maxillofacial Surg 2013. 71:726-733).

Typically, these mini-plates are rectangular or square in shape. For strictly vertical fractures, these plates, and the X-shaped plates described by Lovald (U.S. Pat. No. 8,246,663 B2) work well. However, most mandibular body fractures are actually oblique. When square or rectangular plates are placed obliquely, they have corners which have a poor vertical profile and can encroach upon the tooth roots superiorly, or fall off the inferior mandibular border inferiorly. Such plates also tend to be significantly wider than would be necessary if they were angled in order to better match typical fractures.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Disclosed herein are various embodiments of three dimensional (3D) mini-plates that are oblique in shape, rather than square or rectangular. When a plate as disclosed herein is used to stabilize an oblique mandibular fracture, it will therefore have better vertical profile, and its corners will be less likely to encroach upon tooth roots or the inferior border of the mandible. The oblique plate designs disclosed herein prevent torsion at a mandibular fracture site while keeping a low profile from tooth roots and the inferior mandibular border, and also limit the extent of dissection along the fracture because they better track the course of an oblique fracture.

As many mandibular body fractures are both oblique and within close proximity to the mental foramen and mental nerve, described herein are plates which are adapted to avoid nerve encroachment. The vertical oblique tapered plates herein may be fully reversible, so they can be placed in a variety of orientations. They may have tapered, rounded edges to allow close proximity to the mental nerve, and may additionally have dotted lines to guide the surgeon in cutting away a portion for even increased location to the mental nerves with only limited reduction in plate strength due to the cross-linking of screws.

Figure 1:
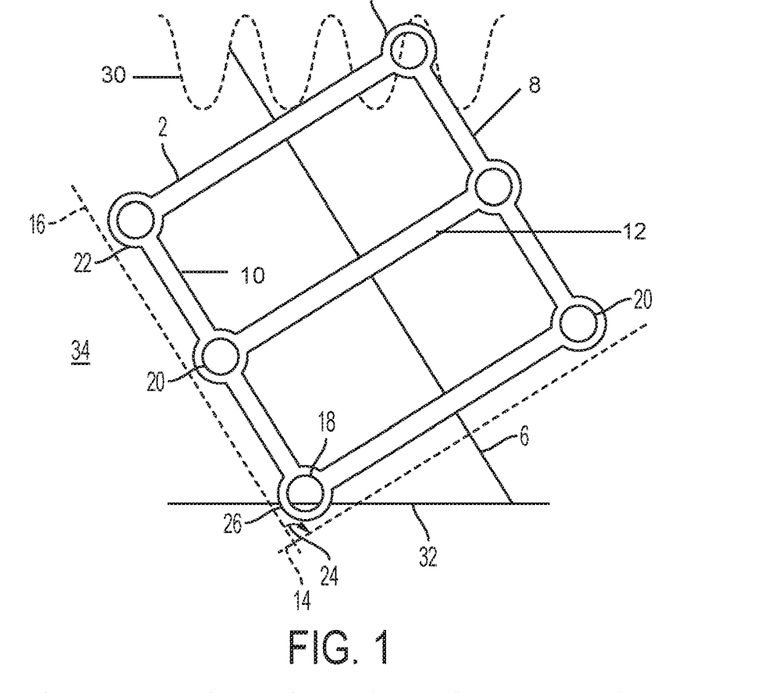
FIG. 1 is a front view of a conventional plate being used to immobilize a fracture in a mandible.

A conventional square three dimensional mini-plate 2 used to immobilize a mandibular fracture 6 is shown in FIG. 1. The mini-plate 2 may have four or six receptacles 18, 20, 22 for screws or other fasteners placed in pairs on opposite sides 8, 10 of a medial portion 12 of the plate 2. The medial portion 12 of the plate 2 is adapted to be placed over a fracture 6 such that the fasteners attach to bone on either side of the fracture, and the fracture is stabilized with the medial portion 12. As shown in FIG. 1, in a conventional square or rectangular 3D mini-plate, a line 14 formed by the outer boundaries of two receptacles 18, 20 at opposing sides of the medial portion 12 of the plate and a line 16 formed by the outer boundaries of receptacles 18, 20, 22 on one side of the plate forms a 90 degree angle 24. Mini-plates are generally oriented so that the receptacles for fasteners are placed on opposite sides of and roughly parallel to the fracture the plate is being used to immobilize so that the fracture can be immobilized by the medial portion of the plate. When a conventional square or rectangular plate is used to immobilize an oblique fracture as shown in FIG. 1, it is placed in a diagonal orientation, and its corners 26, 28 encroach upon tooth roots 30 or the inferior border 32 of the mandible 34.

Figure 2:
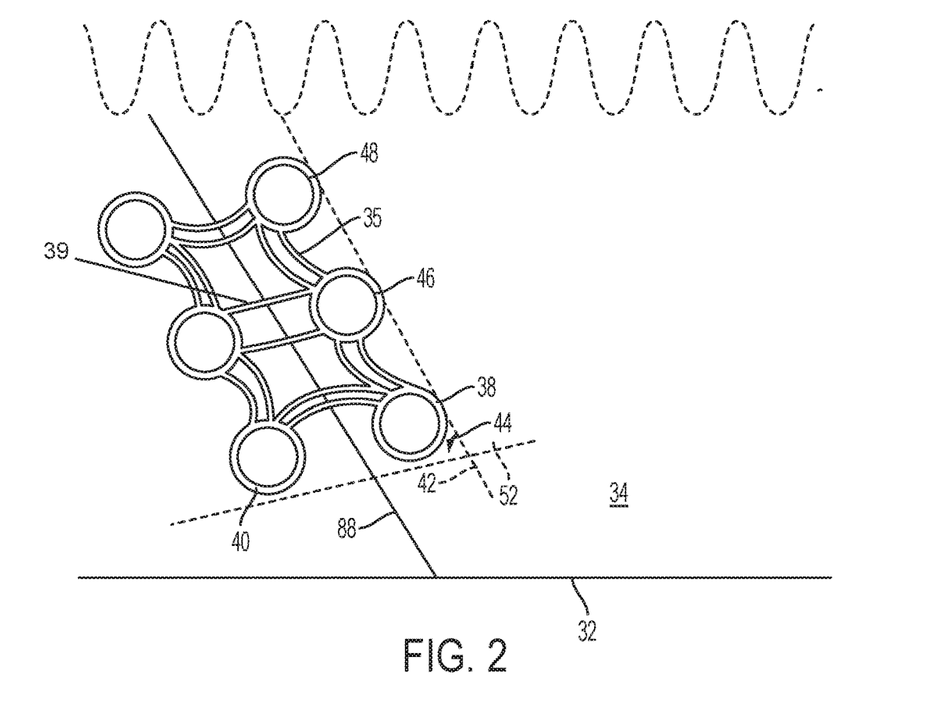
FIG. 2. is a front view of one embodiment of an oblique three-dimensional mini-plate, in accordance with the embodiments disclosed herein, being used to immobilize a fracture in a mandible.

As shown in FIG. 2, in an oblique 3D mini-plate 35 as disclosed herein, pairs of receptacles 38, 40, for fasteners are formed by the body of the plate 35, and positioned in opposition to one another across a medial portion 39. The outer boundaries of the receptacles form the boundaries of the plate. A line 52 formed along the bottom boundary defined by the outer boundaries of receptacles 38, 40 and a line 42 formed along the side boundary as defined by the outer boundary of receptacles 38, 48, 46 intersect to form an angle 44 of between 36 and 60 degrees, and most preferably approximately 45 degrees. Based on the inventor's experience, most mandibular fractures 88 are oblique, and form a similar angle with the lower boundary 32 of the mandible 34. A 3D mini-plate having a geometry that forms an approximately 45 degree angle as described above is well-suited to immobilize oblique mandibular fractures.

Figure 3:
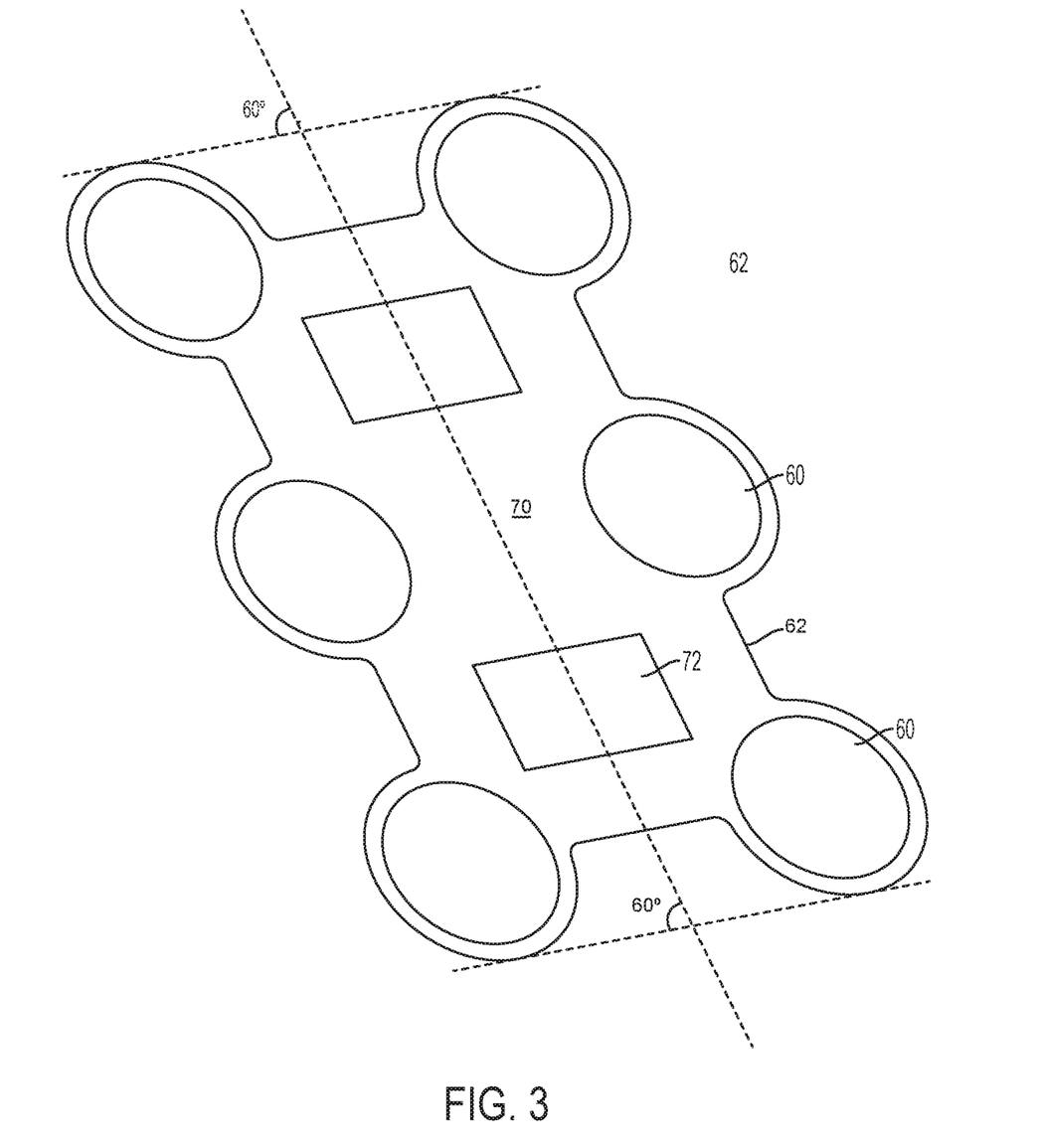
FIG. 3 is a front view of one embodiment of an oblique three-dimensional mini-plate, in accordance with the embodiments disclosed herein.

One embodiment of the oblique plate 62 disclosed herein is shown in FIG. 3. Receptacles 60 for fasteners form holes in the plate 72. As shown in FIG. 3, the plate has an oblique shape as illustrated by lines 64 and 66 and by angle 68, which should most preferably be approximately 45 degrees, and may range from approximately 30 to approximately 60 degrees. Receptacles 60 for screws or other fasteners are placed at each corner of the mini-plate and at approximately the midpoint on each side of the medial section 70. The plate may be a solid shape with internal air spaces 72 as shown in FIG. 3. The plate may be recessed or curved inward around the receptacles as shown by reference number 62 in FIG. 3.

As shown in FIGS. 2 and 4-8, a light, thin plate may be formed from thin elongate strands of rigid material, such as bars or wires. Elongate material can be shaped into rings 80 to define receptacles for fasteners, and the rings can be joined to one other with elongate members 82 and cross members 84 which may also formed from the same material. Two or more cross members 84 made of rigid wire form the medial portion 86 of the plate, which is used to immobilize a fracture 88 as described above. When the plate is formed partially or completely from thin, elongate strands of material, open space surrounds the strands. As described above, the plate is oblique in shape. Such a plate would stabilize a fracture while having minimum contact with the bone to which it is affixed, permitting the bone to be in contact with air, fluid, and tissues. A plate comprised of rigid wire or other elongate, thin, rigid strands of material would be lighter than a solid plate. Cross members 84 and/or elongated members 82 could be formed of two or more strands in order to impart further strength to the structure. A plate formed in this manner could also be easily modified as described below in order to avoid nerves in the mandible.

Figure 4:
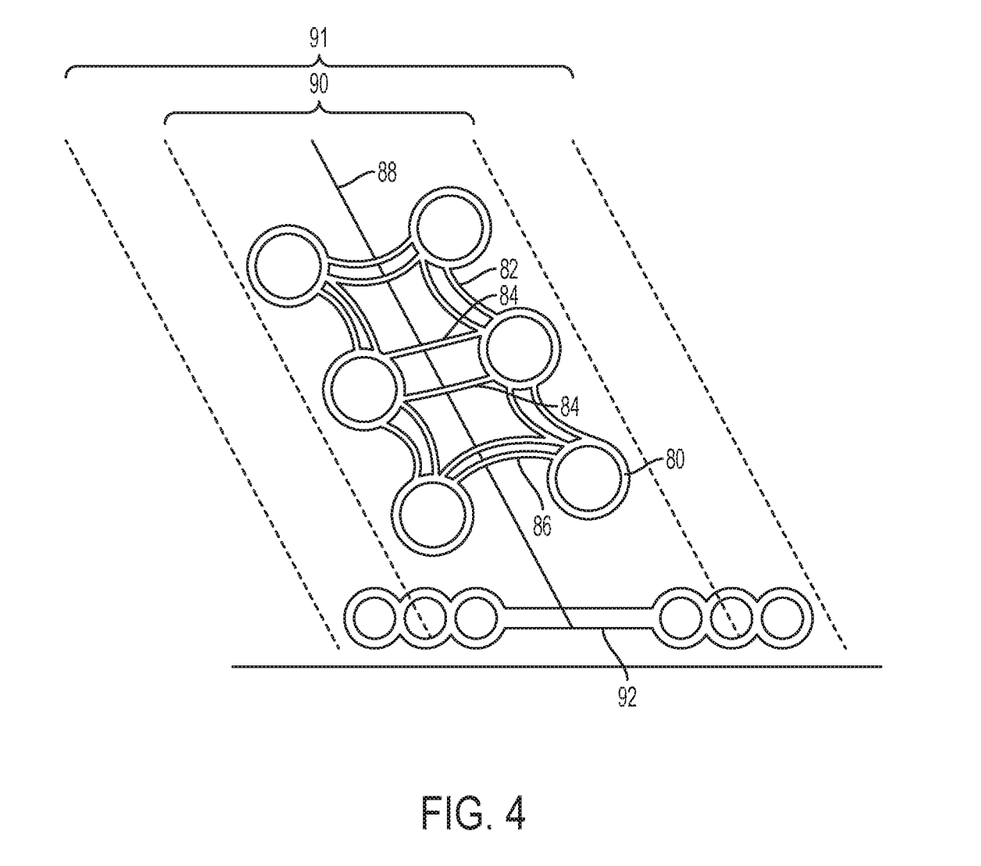
FIG. 4 is a front view of one embodiment of an oblique three-dimensional mini-plate, in accordance with the embodiments disclosed herein, shown above a conventional plate for purposes of comparison.

Plates such as those disclosed herein may be used as follows. Standard approaches to the mandible through soft tissue, preferably from an intra-oral incision are performed. A limited field of dissection 90 as shown in FIG. 4 compared with the dissection 91 required to install a conventional plate 92 is permitted due to the narrowness of the plate. The vertical orientation of the plate is what prevents the twisting of the mandible segments relative to each other despite the use of only a single plate.

Figure 6:
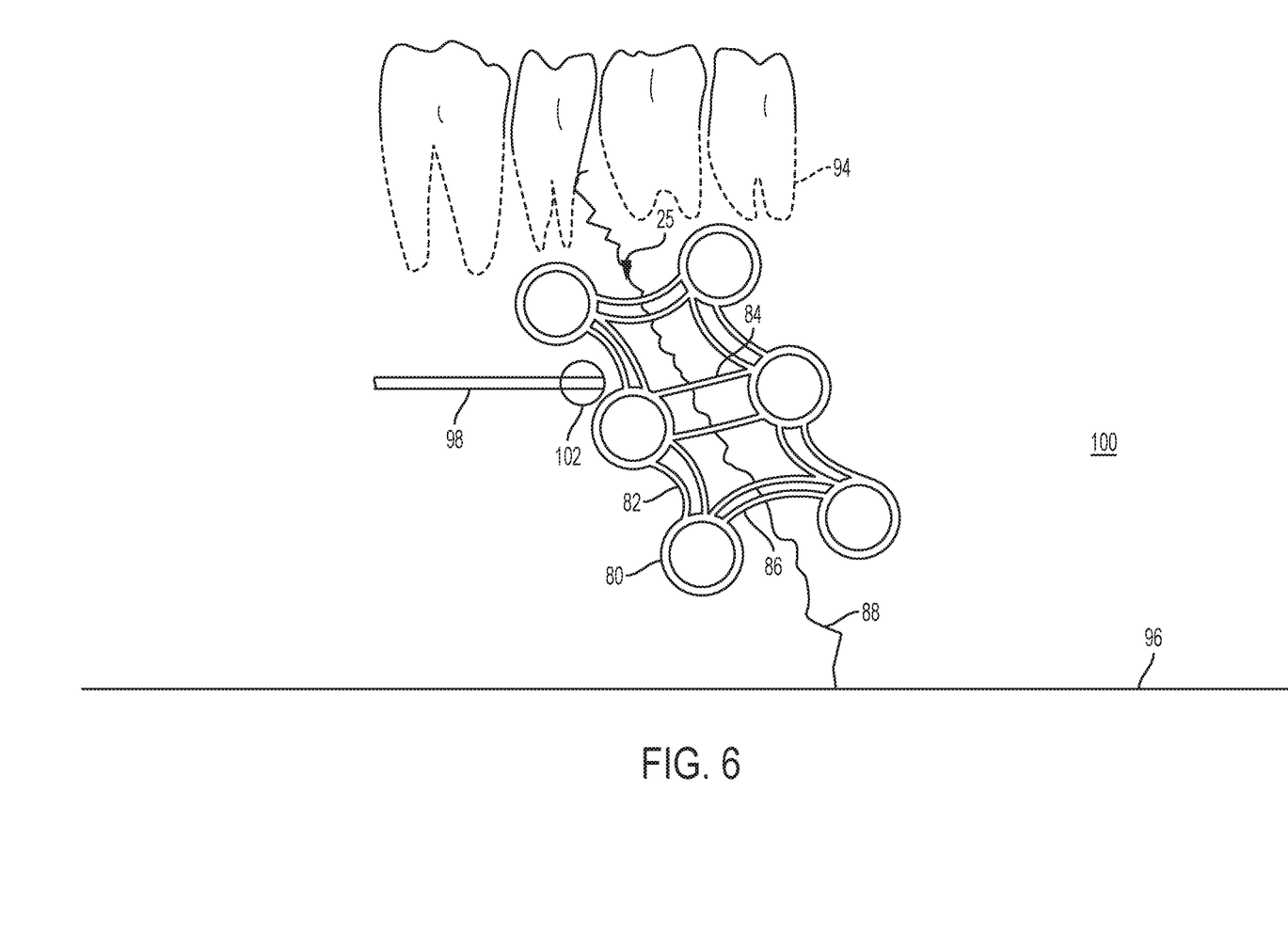
FIG. 6 is a front view of an embodiment of an oblique three dimensional mini-plate being used to repair a fracture in a mandible, in accordance with the embodiments disclosed herein, with the mental nerve also depicted.

The various embodiments of the oblique 3D mini-plate disclosed herein may be reversible, which means a plate can be turned over and used in its opposite orientation. This reversibility, or two-sidedness means a single plate can be used in any direction to match a particular oblique fracture. The plate is oriented so that the flat inferior and superior edges do not overly tooth roots 94 superiorly, or fall off the inferior mandible border 96 inferiorly as shown in FIG. 6. This rhomboid, oblique or trapezoidal shape is what gives a specific advantage to this design over prior square or rectangular 3D plates.

Figure 11:
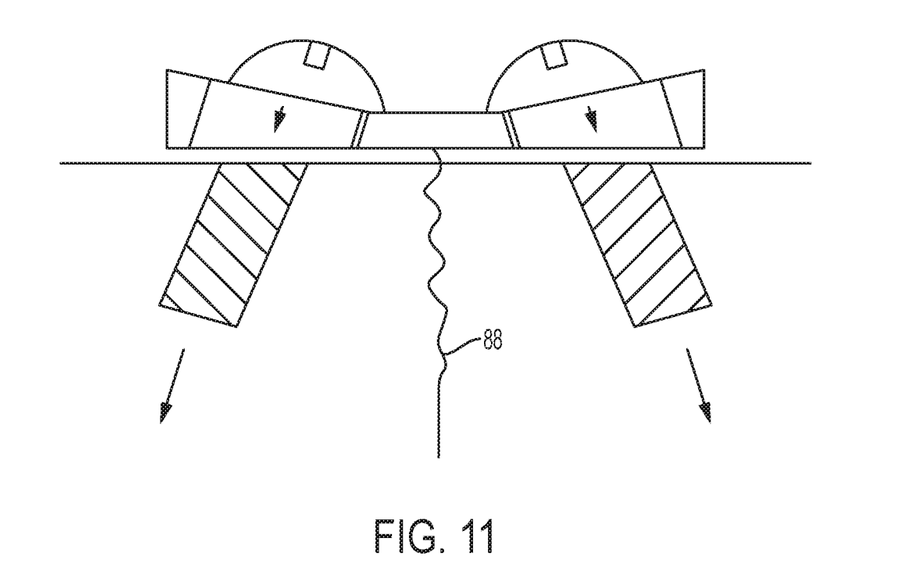
FIG. 11 is a top view of one embodiment of a three-dimensional mini-plate as fastened to a fractured bone, in accordance with the embodiments disclosed herein.

Monocortical screws can be used near the top or superior edge of the plate to avoid injuring tooth roots, and inferiorly, bicortical screws can be used for increased strength, although this can be used interchangeably depending on the situation. As shown in FIG. 11, the receptacles are angled away from the fracture 88 so that the screws will not cause problems at the fracture site, permitting use of this narrow plate. The edges of the plate are raised to permit this angled placement of screws.

Figure 7:
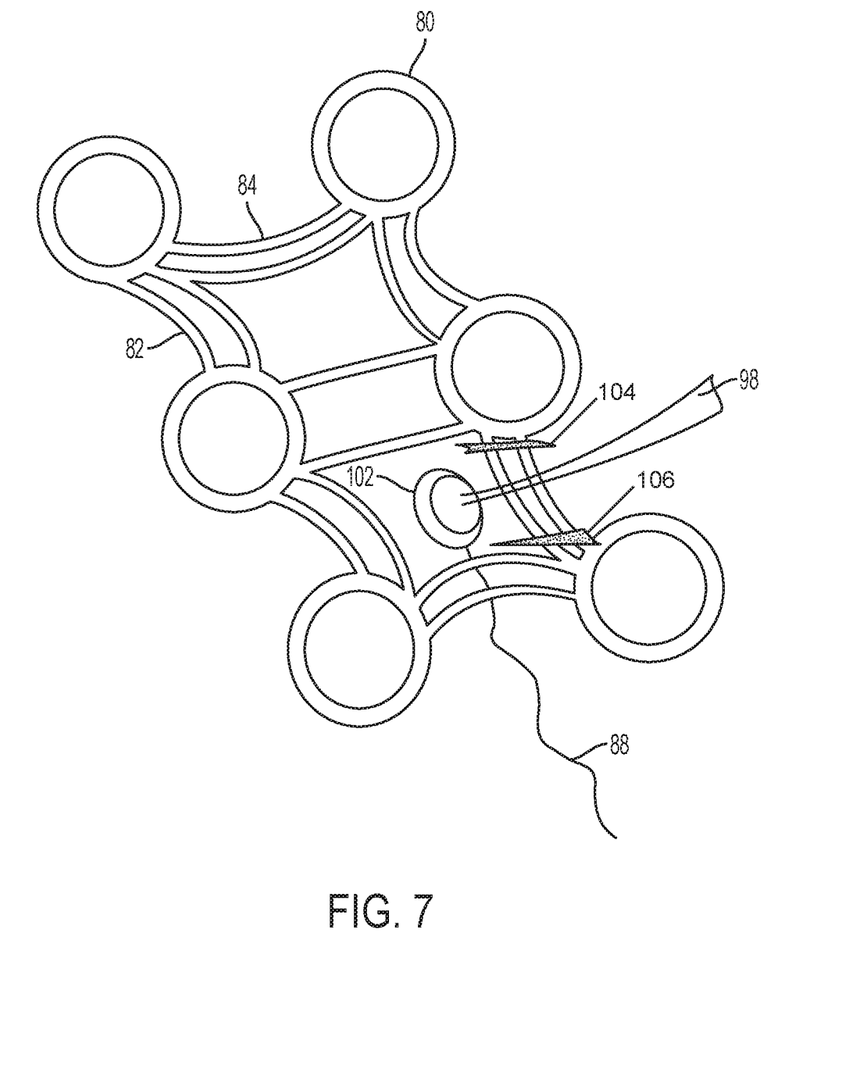
FIG. 7 is a front view of an embodiment of an oblique three dimensional mini-plate being used to repair a fracture in a mandible, in accordance with the embodiments disclosed herein, with the mental nerve also depicted.
Figure 8:
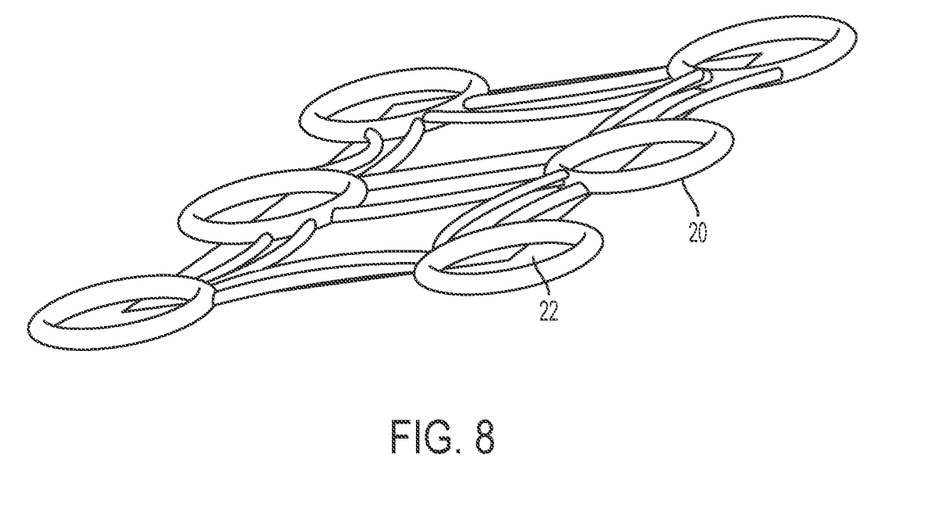
FIG. 8 is a perspective view of one embodiment of an oblique three dimensional mini-plate, in accordance with the embodiments disclosed herein.
Figure 9:
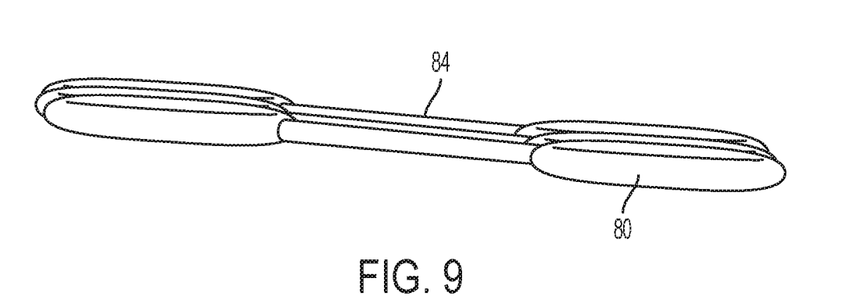
FIG. 9 is a top view of one embodiment of an oblique three dimensional mini-plate, in accordance with the embodiments disclosed herein.

In addition to avoiding the tooth roots above, and the inferior border of the mandible below, the vertical oblique rhomboid plates disclosed herein can be designed or adapted to avoid the nearby sensory nerve branch of the trigeminal nerve 98, known as the mental nerve, which emerges from the mandibular body 100 through the mental foramen 102 as shown in FIGS. 6 and 7.

Figure 5:
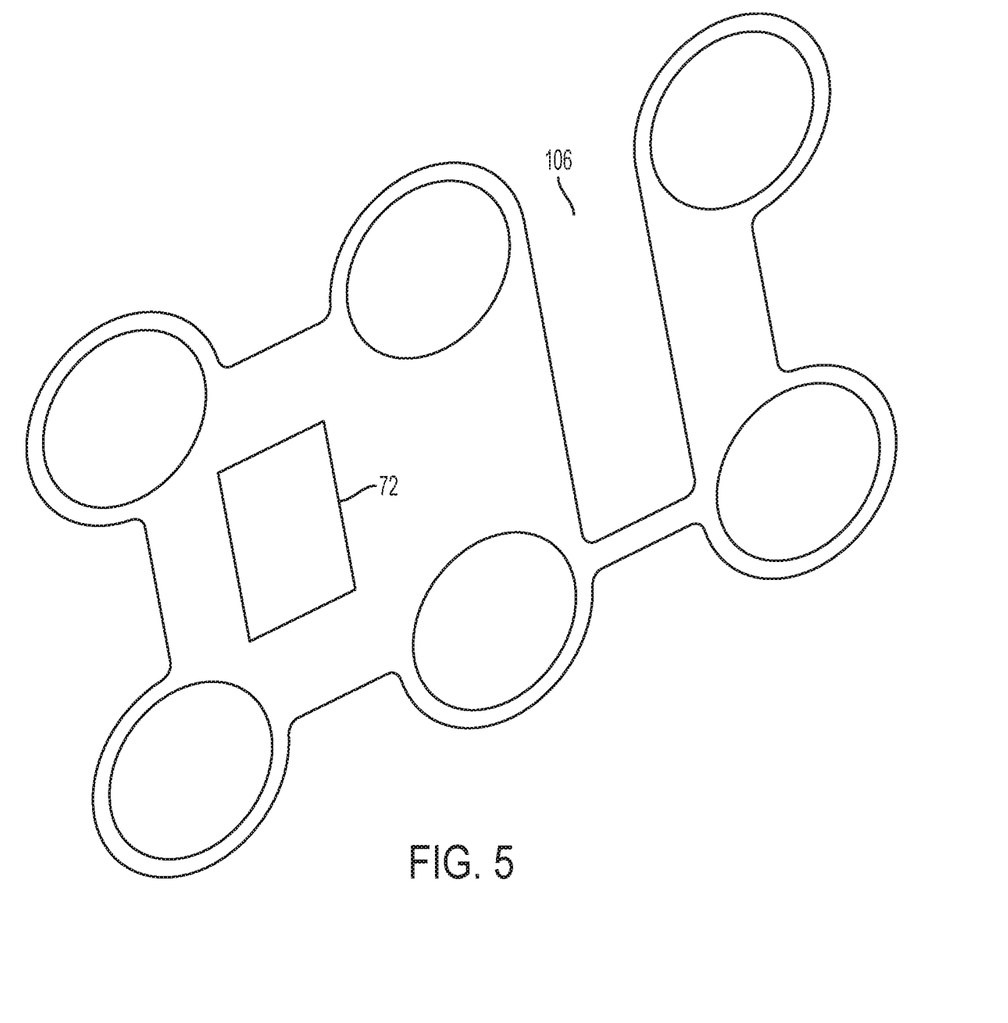
FIG. 5 is a front view of another embodiment of an oblique three-dimensional mini-plate, in accordance with the embodiments disclosed herein.
Figure 10:
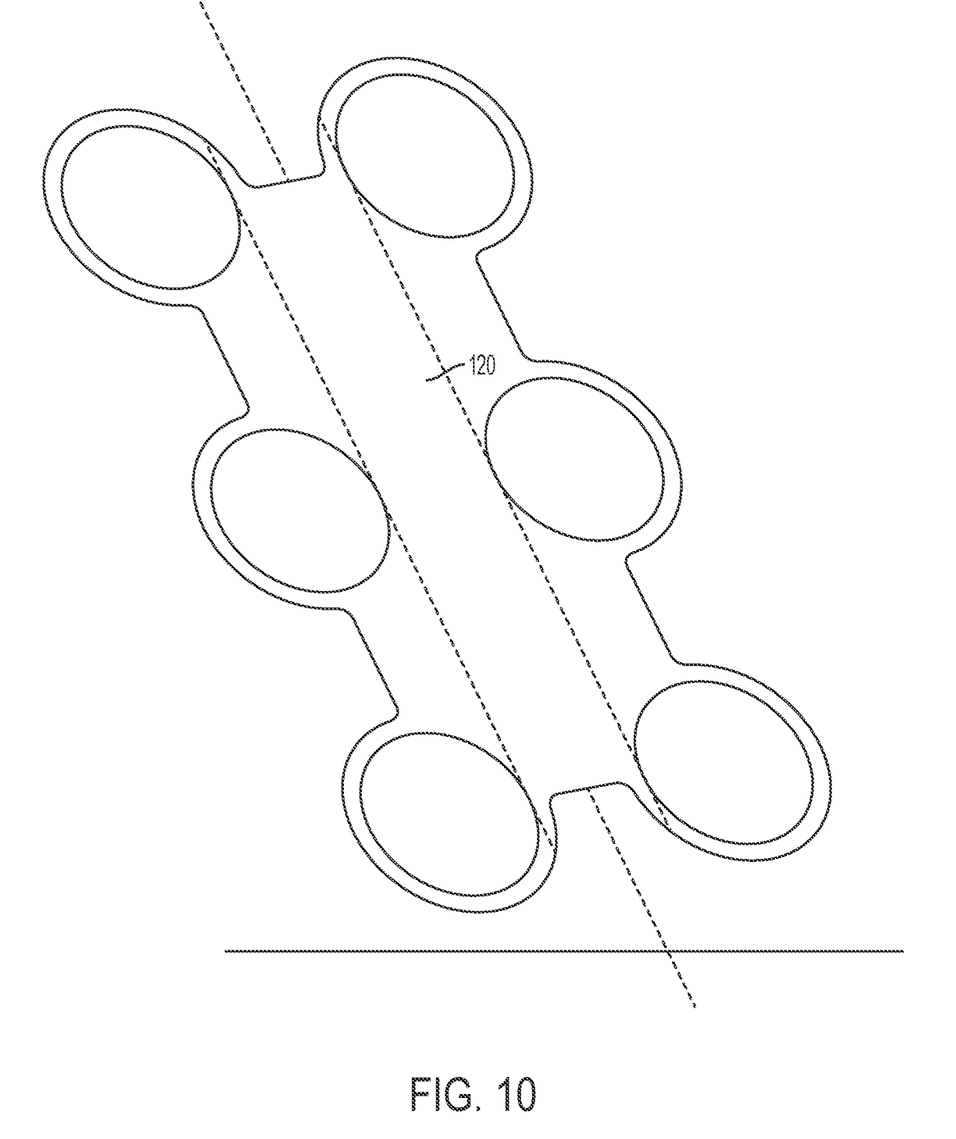
FIG. 10 is a front view of another embodiment of a three dimensional mini-plate, in accordance with the embodiments disclosed herein.

This nerve is a sensory nerve that supplies the lower lip and chin and can be compromised by dissection or hardware placement. Traditionally, the nerve is preserved by placing conventional plates above and below the foramen, thus avoiding it, but particularly the inferior plate can be difficult to access from an intra-oral approach. From an intra-oral approach, the nerve itself as it emerges from the foramen can obstruct the view of the inferior mandibular border. As shown in FIG. 7, an oblique 3D mini-plate can be cut at 104 and 106, and the foramen 102 and nerve 98 can be accommodated within the cut-away section. A bar that abuts the nerve itself can be removed without compromising excessively plate strength. The plate can be adapted to facilitate this with marks that guide a surgeon regarding where to cut the plate. As shown in FIG. 5, a section of a solid plate may be removed, creating a space 106 that can accommodate the nerve and/or the foramen. Alternatively, as shown in FIG. 6, an ultra-narrow plate can be used to avoid proximity to the foramen 102. The oblique 3D plates described can feature a narrower profile than a conventional square or rectangular plate because its oblique geometry permits it to more precisely track an oblique fracture, as described above. As shown in FIG. 10, the medial section of plate 120 may be between 8 and 15 millimeters in width.

It should be noted that the dimensions of the plates disclosed herein can be modified without departing from the spirit and scope of this invention. Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A plate adapted to be affixed to human bone for immobilizing a mandibular fracture,
    the plate having a body formed from thin, elongate strands of a rigid material, the body having an oblique rhomboid shape and comprising a longitudinal axis, a width, a length greater than the width, and three pairs of receptacles connected by a plurality of elongated members and a plurality of cross members,
    wherein the three pairs of receptacles comprise two pairs of corner receptacles and a pair of medial receptacles,
    wherein one corner receptacle is positioned in each of four corners of the plate,
    wherein the pair of medial receptacles are positioned between the two pairs of corner receptacles,
    wherein one receptacle in each pair of corner and medial receptacles is positioned linearly in opposition to the other receptacle in each pair along the width of the body and is separated from the other symmetrically about the longitudinal axis of the body by one of the cross members of the body at a medial portion of the body, and wherein at least one of the corner receptacles and an adjacent medial receptacle are separated from each other along the length of the body by one of the elongated members of the body,
    wherein the body further comprises a first axis positioned along an outermost edge of both receptacles in one pair of corner receptacles a second axis positioned along an outermost edge of each of two corner receptacles and one medial receptacle a third axis positioned along an outermost edge of each of two other corner receptacles and a second medial receptacle, and a fourth axis positioned along an outermost edge of both receptacles in the other pair of corner receptacles, wherein an intersection of the first axis and the second axis forms a first angle that is between 30 and 60 degrees,
    and wherein an intersection of the third axis and the fourth axis forms a second angle that is between 30 and 60 degrees.

2. The plate of claim 1 wherein the first angle is between 40 and 50 degrees.

3. The plate of claim 1 wherein the second angle is between 40 and 50 degrees.

4. The plate of claim 1 wherein the medial portion is between 8 and 15 mm in width.

5. The plate of claim 1 wherein the plurality of elongated members comprises two or more elongated members and wherein the plurality of cross members comprises two or more cross members.

6. The plate of claim 5 wherein the body further includes one or more open spaces defined by the two or more elongated members and the two or more cross members.

7. A method of immobilizing an oblique fracture in a human mandible, comprising:
    providing a plate according to claim 1, and
    affixing the plate to the human mandible by inserting a fastener through each receptacle and into the mandible, wherein the medial portion of the body is in contact with the fracture and one receptacle of each pair of receptacles is located on an opposing side of the fracture from the other receptacle.

* * * * *